US 6,534,094 B2

(12) United States Patent
Moyano et al.

(10) Patent No.: US 6,534,094 B2
(45) Date of Patent: Mar. 18, 2003

(54) MANUFACTURING PROCESS OF MICROCAPSULES FOR SUSTAINED RELEASE OF WATER SOLUBLE PEPTIDES

(75) Inventors: Nora Moyano, Entre Rios (AR); Jose Iturraspe, Entre Rios (AR); Jose Lucio Nunez, Entre Rios (AR)

(73) Assignee: Eriochem S.A. (AR)

(*) Notice: Subject to any disclaimer, the term of this patent is extended or adjusted under 35 U.S.C. 154(b) by 6 days.

(21) Appl. No.: 09/848,623

(22) Filed: May 3, 2001

(65) Prior Publication Data

US 2002/0031553 A1 Mar. 14, 2002

(30) Foreign Application Priority Data

May 3, 2000 (AR) .......................................... 000102102

(51) Int. Cl.[7] .............................. A61K 9/16; B01J 13/02
(52) U.S. Cl. ........................ 424/491; 264/4.1; 264/4.3; 264/4.33; 264/4.4; 264/4.6; 424/460; 424/489; 424/492; 428/402.21; 526/65; 526/66; 526/71; 514/963; 514/965
(58) Field of Search .................. 264/4.1, 4.3, 4.33, 264/4.4, 4.6; 424/460, 489, 491, 492; 428/402.21; 526/65, 66, 71; 514/963, 965

(56) References Cited

U.S. PATENT DOCUMENTS

| | | | |
|---|---|---|---|
| 2,800,457 A | 7/1957 | Green et al. ................ 252/316 |
| 3,297,033 A | 1/1967 | Schmitt et al. .......... 128/335.5 |
| 3,691,090 A | 9/1972 | Kitajima et al. ............ 252/316 |
| 3,773,919 A | 11/1973 | Boswell et al. ............... 424/19 |
| 3,839,297 A | 10/1974 | Wasserman et al. ... 260/78.3 R |
| 3,960,757 A | 6/1976 | Morishita et al. ........... 252/316 |
| 4,010,125 A | 3/1977 | Schally et al. ................ 260/8 |
| 4,024,248 A | 5/1977 | Konig et al. ................ 424/177 |
| 4,100,274 A | 7/1978 | Dutta et al. .................. 424/177 |
| 4,234,571 A | 11/1980 | Nestor et al. ................ 424/177 |
| 4,273,920 A | 6/1981 | Nevin .......................... 528/361 |

(List continued on next page.)

FOREIGN PATENT DOCUMENTS

| | | |
|---|---|---|
| CH | 653553 | 1/1986 |
| EP | 0765659 | 4/1997 |
| FR | 1362933 | 6/1964 |
| FR | 1362934 | 6/1964 |
| WO | WO 95/13799 | 5/1995 |
| WO | WO 98/35654 | 8/1998 |
| WO | WO 00/72955 | 12/2000 |

OTHER PUBLICATIONS

Hanes, Justin, et al., "New Advances in Microsphere–based Single–dose Vaccines," *Advanced Drug Delivery Reviews* 28 (1997) : 97–119.

(List continued on next page.)

*Primary Examiner*—Samuel A. Acquah
(74) *Attorney, Agent, or Firm*—Nelson Mullins Riley & Scarborough

(57) ABSTRACT

A process for the manufacturing of microcapsules for sustained release of water soluble peptides, with adjustable release periods of between 1 to 18 weeks. The microcapsule wall are made of a biodegradable polymer. The process is based on the formation of an intermediate complex water/oil/water emulsion. By evaporating the solvent in the emulsion by pressure reduction the microcapsules consolidate, retaining the active peptides in the polymeric matrix. The process produces the complex emulsion in a two mixer, continuous operation. In the first mixer a water/oil emulsion is formed and it is used to form the complex emulsion in the second mixer. By operating in a continuous manner, the process overcome the problems found in existing processes regarding particle size distribution, material losses and process control, among others.

47 Claims, 5 Drawing Sheets

U.S. PATENT DOCUMENTS

| | | | | |
|---|---|---|---|---|
| 4,652,441 | A | 3/1987 | Okada et al. | 424/19 |
| 4,675,189 | A | 6/1987 | Kent et al. | 424/490 |
| 4,835,139 | A | 5/1989 | Tice et al. | 514/15 |
| 4,954,298 | A | 9/1990 | Yamamoto et al. | 264/4.6 |
| 5,271,945 | A | 12/1993 | Yoshioka et al. | 424/489 |
| 5,330,767 | A | 7/1994 | Yamamoto et al. | 424/497 |
| 5,476,663 | A | 12/1995 | Okada et al. | 424/423 |
| 5,540,937 | A | 7/1996 | Billot et al. | 424/489 |
| 5,611,971 | A | 3/1997 | Maedera et al. | 264/4.1 |
| 5,622,657 | A | 4/1997 | Takada et al. | 264/4.32 |
| 5,651,990 | A | 7/1997 | Takada et al. | 424/497 |
| 5,733,567 | A | 3/1998 | Arola et al. | 424/426 |

OTHER PUBLICATIONS

Kondo, Asaji, *Microcapsule Processing and Technology.* Ed. J. Wade Van Valkenburg. New York, NY: Marcel Dekker, Inc., 1979. 106–120.

*Controlled Release Systems: Fabrication Technology.* Ed. Dean Hsieh, Ph.D. Boca Raton, FL: CRC Press, Inc., 1988. 83–108.

Maa, Yuh–Fun, et al., "Liquid–liquid Emulsification by Rotor / Stator Homogenization," *Journal of Controlled Release* 38 (1996): 219–228.

O'Donnell, Patrick B., et al., "Preparation of Microspheres by the Solvent Evaporation Technique," *Advanced Drug Delivery Reviews* 28 (1997): 25–42.

Ogawa, Yasuaki, et al., "Controlled–Release of Leuprolide Acetate from Polylactic Acid or Copoly(Lactic/Glycolic) Acid Microcapsules: Influence of Molecular Weight and Copolymer Ratio of Polymer," *Chem. Pharm. Bull.* 36 (1988): 1502–1507.

Ogawa, Yasuaki, et al., "In Vivo Release Profiles of Leuprolide Acetate from Microcapsules Prepared with Polyactic Acids or Copoly(Lactic/Glycolic) Acids and in Vivo Degradation of These Polymers," *Chem. Pharm. Bull.* 36 (1988): 2576–2581.

Okada, Hiroaki, et al., "Drug Delivery Using Biodegradable Microspheres," *Journal of Controlled Release* 28 (1994): 121–129.

Okada, Hiroaki, "One– and Three–Month Release Injectable Microspheres of the LH–RH Superagonist Leuprorelin Acetate," Advance Drug Delivery Reviews. 28 (1997): 43–70.

Okada, Hiroaki, "Preparation of Three–Month Depot Injectable Microspheres of Leuprorelin Acetate Using Biodegradable Polymers," *Pharmaceutical Research*. vol. 11, No. 8 (1994): 1143–1147.

Okada, Hiroaki, et al., "Sustained Pharmacological Activities in Rats Following Single and Repeated Administration of Once–A–Month Injectable Microspheres of Leuprolide Acetate," *Pharmaceutical Research*. vol. 8, No. 5 (1991): 584–587.

Redding, T.W., et al., "Inhibition of Prostate Tumor Growth in Two Rat Models by Chronic Administration of D–Trp[6] Analogue of Luteinizing Hormone–Releasing Hormone," *Proc. Natl. Acad. Sci.* vol. 78, No. 10 (1981): 6509–6512.

Sanders, L.M., et al., "Controlled Release of a Luteinizing Hormone–Releasing Hormone Analogue from Poly(d,I – lactide–co–glycolide) Microspheres," *Pharm. Sci.*, 73 (1984): 1294–1297.

Senior, Judy H., et al., ed., *Sustained–Release Injectable Products*. Denver, Colorado: Interpharm Press, 2000. 430–456.

Visscher, G.E., et al., "Effect of Particle Size on the in vitro and in vivo Degradation Rates of Poly(DL–lactide–co–glycolide) Microcapsules," *Journal of Biomedical Materials Research* 22 (1988): 733–746.

Whateley, Tony L., ed., *Microencapsulation of Drugs*. Switzerland: Harwood Academic Publishers, 1992.

MANUFACTURING PROCESS OF MICROCAPSULES FOR SUSTAINED RELEASE OF WATER SOLUBLE PEPTIDES

FIELD OF THE INVENTION

The present application claims the benefit of Argentina Application 000102102 filed May 3, 2000 and is incorporated herein by reference thereto.

The invention is related to continuous pharmacotechnical methods for the manufacturing of microcapsules of biodegradable and biocompatible polymeric materials that incorporate an active peptide in the polymer matrix by the formation of complex emulsions of the water/oil/water type (W/O/W). The process of the invention was develop to obtain these microcapsules in sterile injectable form thus allowing for the controlled administration, for adjustable release periods of between 1 to 18 weeks, of water soluble or dispersible drugs that are used for the treatment of neoplastic, gynaecological and other diseases. Thus, the invention is in the field of pharmacology and, particularly, it relates to pharmacotechnical processes for the manufacturing of injectable, controlled release medicines.

BACKGROUND OF THE INVENTION

Since the pioneer work on encapsulation by coacervation conducted by B. K. Green (U.S. Pat. No. 2,800,457) directed to the development of copy papers, a number of publications and books have been written on microencapsulation of natural or synthetic substances into polymeric walls and their application in the controlled release of those substances (Microcapsule Processing and Technology, Asaji Kondo, 1979, Marcel Dekker). The gradual release of substances in controlled time intervals is important in pharmaceuticals drugs, foods, agrochemicals, fertilizers, and other products. A notable development, according to the number of publications observed in the recent years, took place in the area of microencapsulation of active pharmaceutical ingredients (Microspheres and Drug Therapy, Ed. Stanley S. Davis and others, 1984, Elsevier; Controlled Release Systems: Fabrication Technology, Vol I and II, Ed. Dean Hsieh, 1988, CRC Press, Inc.; Polymeric Drugs and Drugs Delivery Systems, Ed. Richard L. Dunn, 1991, ACS Symposium Series 469; Microencapsulation of Drugs, T. L. Whateley, 1992, Harwood; and Sustained Release Injectable Products, Ed. J. Senior and M. Radomsky, Interpharm Press, Denver, Colorado, USA, 2000). This complex physicochemical process has become a specialty field on its own rights.

In the area of pharmaceutical substances, clinical studies have shown that in many cases better therapeutic or pharmacological effects can be obtained by continuous infusion of the drug than when the same drug is administered by conventional methods, either in injectable, oral or other forms. Thus, it is necessary to consider using technologies for the prolonged release of active ingredients, which also include injection, oral, and other forms to administered the drug such as subcutaneous implants.

Generally, the substitution of a slow drug release method for a conventional one produces less pronounced collateral effects. These effects correlate to drug concentration peaks in the organism that occur when the minimum required active agent concentration is exceeded. One of those prolonged release methods is the use of microcapsules of polymers containing active agents such as polypeptides, proteins, hormones, nucleotides, and chemotherapy drugs, among others. Once the microcapsules are administered to the organism, drugs may be released by diffusion through a semi permeable wall in some cases, by wall dissolution in others, or by multiple mechanisms that include mainly the biodegradation of the encapsulating polymer in the living tissues into biocompatible fractions that follow a metabolic route for absorption or elimination. These polymer biodegradation processes cause, therefore, the slow dosing of the active ingredient.

Microcapsules based on re-absorbable and/or biodegradable polymers or co-polymers, have been the subject of extended research on manufacturing materials and methods, as well as on administration routes. Currently, microcapsules are increasingly applied in the administration of biotechnology products, including water soluble, slightly soluble, or insoluble substances. There are several administration routes for this particular type of microcapsules, depending on the drug to be released. The microcapsules can be adapted to injectable administration as well as to the administration to the gastrointestinal system, nasal tissues and other access routes.

Provided they degrade into biocompatible residues, a large number of polymers with a main hydrophobic chain may be used to form the microcapsule wall. Occasionally, the polymers may require a special level of purification. Among others, generally used biodegradable polymers are: poly(d,l-lactic) acid; poly(d,l-lactic-glycolic) copolymer; poly(caprolactones); poly(hydroxybutirate); poly (orthoesters); and poly(anhydrous) as well as mixtures of these and other polymers (Polymeric Drugs and Drug Delivery Systems, Ed. Richard L. Dunn, 1991, ACS Symposium Series 469, p. 15–20).

Poly(d,l-lactic-glycolic) acid, a d,l-lactic acid and glycolic acid copolymer, generally known as PLGA, and the homopolymer of d,l-lactic acid, poly(d,l-lactic) acid, generally known as PLA, have been used since 1973 as polymers for medicine microcapsules. Among others, examples of its use are: the microencapsulation of a narcotic antagonist like naltrexone (J. H. R. Woodlnad et al., J. Med. Chem., vol 16, 897, (1973); S. E. Harrigan et al., Midl. Macromol. Monogr., vol 5 (Polym. Delivery Systems), vol 91 (1978)); of anaesthetic substances (N. Wakiyama et al., Chem. Pharm. Bull., vol 30, 3719, (1982)), and of steroids (D. L. Wise et al., J. Pharm. Pharmacol., vol 32, 399, (1980)). We can specially mention the use of PLGA 50:50 and 69:31 (mole ratio of lactic acid to glycolic acid) in the microencapsulation of nafarelin acetate, an analog of the luteinizing hormone release hormone (LH-RH) (L. M. Sanders et al., J. Pharm. Sci., vol 73, 1294–1297, (1984)). Currently, it is completely accepted the use of PLGA and PLA as biocompatible polymers that are degradable to toxically acceptable products that are eventually eliminated from the body (D. H. Lewis, Biodegradable Polymers as Drug Delivery Systems, Ed. M. Chasin et al., Marcel Dekker, New York, NY, pp 1–42, 1990).

PLA or PLGA of controlled molecular weight are obtained by polycondensation of cyclic dimers of the lactic and glycolic acids, known as lactide and glycolide. There is an extensive literature on synthesis and purification methods of PLA and PLGA with molecular weights of 25000 Daltons or less. Among direct polycondensation procedures it can be mentioned those that are carried out without a catalyst, those that use a metallic catalyst as described in, among others, U.S. Pat. Nos. 3,297,033, 3,773,919 and 3,839,297, and those that use acid catalysts such as ionic exchange resins as taught in U.S. Pat. No. 4,273,920.

Slow release microcapsules are known in the administration of hormones, antibiotics, anti-inflammatory substances, antitumoral drugs, antihypertensive drugs, antipyretics, vasodilators, antiallergic agents, and analgesics, where PLGA o PLA is the constitutive biodegradable wall material.

Of particular interest for the purpose of the present invention are microcapsules containing biologically active substances that are either water soluble or can form a suspension in an aqueous phase. Among the water soluble drugs of interest are active peptides and specially hormones. One water soluble hormone of particular interest is leuprolide acetate, which was synthesized almost simultaneously by J. A. Vilchez-Martinez et al., (Biochem. Biophys. Res. Commun. 59, 1226, (1974)) and by Fujino et al. (M. Fujino et al., Biochem. Biophys. Res. Commun. 60, 406–413, (1974)), and it is the first superactive agonist of the luteinizing hormone release hormone (LH-RH), with approximately 10 times the biological activity of LH-RH. It has been used for the treatment of hormone dependent tumors in prostate (T. W. Redding et al., Proc. Nat. Acad. Sci. USA, vol 78, 6509–6512, (1981)) and breast cancers (E. S. Johnson et al., Science, vol. 194, 329–330, (1976)), endometriosis (D. R. Meldrum et al. J. Clin. Endocrinol. Metab., vol. 54, 1081–1083, (1982)) and uterine fibrosis (M. Filicori et al., Am. J. Obstet. Gynecol., vol. 152, 726–727, (1985)).

In studies conducted by H. Okada et al. on vaginal absorption of leuprolide in rats, it was observed that constant levels of the drug in the blood produce higher castration rates than the intermittent and pulsating administration of this drug. It was then thought that a slow release injection should produce optimal therapeutic results (H. Okada et al., J. Pharm. Dyn., vol. 6, 512–522, (1983)). This thought originated the development of the so-called depot injection method, that allows for a leuprolide acetate release period of up to 120 days (H. Okada et al. Jap. Patent Appl. No. 207760, U.S. Pat. No. 4,652,441; Y. Ogawa et al. Chem. Pharm. Bull., vol 36, 1095, (1988)). Other hormones of particular interest for the present invention, agonists of the luteinizing hormone releasing hormone (LH-RH) are: goserelin acetate (U.S. Pat. No. 4,100,274), buserelin acetate (U.S. Pat. No. 4,024,248), triptorelin acetate (U.S. Pat. No. 4,010,125) and nafarelin acetate (U.S. Pat. No. 4,234,571)

A number of methods have been developed for the microencapsulation of active ingredients into biodegradable and non-biodegradable polymers. Among these methods, three main types predominate: those based on emulsion/separation of phases; those based on "spray" drying; and those based on evaporation of the solvent of an aqueous or organic vehicle phase.

In emulsion/separation of phase techniques, an aqueous solution of the drug, or the drug in powder state, is dispersed into an organic solution containing the polymer. Once the emulsion is formed, a coacervation agent is added, generally a vegetal or mineral oil, which induces the formation containing the active ingredient. See, e.g., U.S. Pat. Nos. 4,675,189 and 4,835,139. These methods have the disadvantage of using large amounts of solvents and oils. In addition, the microcapsule formation stage also depends on the quantities of polymer, solvent, and coacervation agent used. An additional undesirable effect is the tendency of the particles to adhere to each other during the manufacturing process.

Encapsulation by "spray" drying consists in initially preparing an aqueous phase containing the active agent in solution or suspension. This aqueous medium is dispersed into an organic phase that contains the polymer to produce a water/oil (W/O) type emulsion. This emulsion is pulverized in a hot air flow in a drying equipment. The microcapsules are formed by the evaporation of the organic solvent. U.S. Pat. No. 5,622,657 teaches one application of this method for the semi-continuous manufacturing of peptide microcapsules, including leuprolide acetate. The patent teaches the formation of microspheres by "spray" drying of a water/oil emulsion and, simultaneously, spraying from an auxiliary nozzle an aqueous solution containing a substance that contributes to prevent particle adherence during their formation.

Procedures based on solvent evaporation of an aqueous or organic phase are the most common one in microcapsule manufacture. The basic technique consists in dispersing the drug in a polymer solution in an organic solvent. The active ingredient may be in powder form or dissolved in a solvent that is emulsionable in the polymer solution. This first dispersion is then emulsioned in a second solvent, which is called the vehicle solvent, that is non miscible with the solvent in the polymer solution. This last solvent is then evaporated in a subsequent step of the process.

There are a variety of techniques based on solvent evaporation that were developed for the microencapsulation of water soluble and non soluble substances.

U.S. Pat. No. 3,691,090 teaches the encapsulation of water soluble substances, including medicines, where these substances are dispersed into an organic solvent which is either miscible or partially miscible in water. The polymer is dissolved in that solvent and the organic phase is emulsified into an aqueous medium containing an inorganic salt to prevent solubilization of the organic solvent. The resulting oil/water (O/W) emulsion contains oily microspheres of polymer containing the active substance. Microcapsules are consolidated by organic solvent evaporation.

U.S. Pat. No. 3,960,757 teaches a method of encapsulation of water insoluble or slightly soluble medicines consisting in dissolving or dispersing the active substance into a polymer solution in an organic solvent which is almost insoluble in water. The organic solvent must have a vapor pressure greater than water. The organic phase is emulsified in a vehicle consisting of an aqueous solution of a hydrophilic colloid or a surfactant agent, to produce an oil/water (O/W) two-phase system. The organic solvent is then removed by evaporation and the microcapsules consolidate. The patent also teaches the use of gelatin, polyvinyl alcohol (PVA), carboximethylcellulose, and other substances, as hydrophilic colloids. The patent teaches to use as organic solvent to dissolve the polymer certain chloroalkanes such as dichloromethane, ethylene chloride, chloroform, and others. The polymers used in the taught process are of the hydrophilic type.

U.S. Pat. No. 5,540,973 teaches a process to prepare microspheres containing the LH-RH hormone and its analogs in a biodegradable and water insoluble polymer matrix. According to the taught process, the polymer is dissolved in a first organic solvent, and then the hormone is dispersed in that solution by agitation. Then, this first solvent is evaporated to dryness, and the residual mass is contacted with a second solvent where the polymer dissolve, but not the active drug which stays in suspension. The final stage comprises the preparation of an oil/water (O/W) emulsion, the addition of a surfactant agent, and the evaporation of the second solvent to cause the formation of microspheres.

Of particular interest for the present invention is the procedure of microencapsulation that uses a in-liquid drying process, or complex emulsion method, as the method was called by Asaji Kondo (Microcapsule Processing Technology, 1979, Marcel Dekker, Ch. 10, p. 106), and more specifically, the in-water drying method. See Japanese Patents Nos. JP39-28744, JP42-13703, and JP43-10863 and French Patent No. FR1362933. This method consists in first preparing an aqueous phase in oil emulsion (W/O) and then forming for encapsulation a second emulsion ([(W/O)/W] type emulsion) by dispersing the first water in oil emulsion in a second aqueous phase.

This method has a number of advantages: it doesn't need pH adjustments, the use of a significant heat source, or any special reactant. Thus, chemically unstable materials can be microencapsulated without substantial degradation. Other advantages, that are dependent on the degree of control that mat be had on the physicochemical conditions of the preparation, are: better yields of microcapsules free from agglomeration, and better efficiency in active ingredient encapsulation, compared to the other methods described above. Further, this process can be used to prepare small batches (0.25 to 1.0 g) of active ingredient batches, useful when the active ingredient is very expensive. In addition, the process can be easily scaled-up to process larger amounts (10 to 100 g) of active ingredient.

Essentially, microencapsulation by in-water drying of complex emulsions consists in preparing a first water in oil type emulsion (W/O) by dispersing a volume V of an aqueous solution of the active material into an eight times V volume of a solvent partially or totally immiscible in water, where the polymer that will form the microcapsule wall was dissolved. This solvent must have a boiling point lower, and a vapor pressure greater than water, so it can be evaporated in presence of water. Separately, it is prepared a 40 times V volume of an aqueous solution containing a stabilizer or protective colloid. Microencapsulation is caused by agitating the last solution while adding the (W/O) dispersion, to obtain a total volume approximately equal to 50 times V of a water in oil in water double emulsion [(W/O)/W]. This system is stable. The fluid microcapsules are made of an organic solution of the polymer containing dispersed in its interior micro- and nano-drops of an aqueous solution of the active ingredient. This polymer organic solution is emulsified in the external aqueous phase. When the organic solution polymer is dried by heating and/or reduced pressure, the polymeric matrix that forms the microcapsule becomes hard, and the aqueous micro-drops or nano-drops of the active ingredient remain trapped into the microcapsule.

The microcapsule size and stability are influenced mainly by factors such as (W/O) emulsion viscosity, local agitation intensity, temperature, and the addition of some additive substances in the aqueous phases. Using this method microcapsules of 1 to several hundred of microns in diameter may be prepared. It is convenient, in some applications, to add to the first (W/O) emulsion certain hydrophilic substances such as, among others, albumin and gelatin, dissolved in water to act as retention agent of the active substances. (French Patent No. FR1362933; Japanese Patent No. JP43-10863). These hydrophilic substances contribute to stabilizing the (W/O) emulsion by preventing micro-drop coalescence. Further, it is advisable, during preparation of the second [(W/O)/W] emulsion, to dissolve in the external aqueous phase a hydrophilic protective colloid such as gelatin or polyvinyl alcohol (PVA) to function as stabilizer. (French Patent No. FR1362933; Japanese Patent No. JP42-13703; A. Kondo, Ind. Chem. (Japan), 72 (2), 493 (1969)). These colloids must be only slightly soluble in the organic solvent of the oily phase where the first (W/O) emulsion is produced (W/O). If no protective colloid is used, the active agent entrapment in the microcapsules is notably reduced, and a microcapsule inversion may occur. This is a particular situation where the aqueous internal core is released to the external aqueous medium, and only empty polymer microspheres are formed. The process results depend strongly on the selection and specific molecular properties of the hydrophilic protective colloid used in the second emulsion as well as the active ingredient retention substance used in the first emulsion. However, patents and scientific publications, although mentioning a number of possible substances that can be used for these purposes, do not give any significant specifications about these substances.

A disadvantage of in-water drying is that it takes a long time to eliminate the solvent from the polymer solution, which includes the micro-drops containing the active ingredient. If the solvent is removed too rapidly, little orifices and bubbles may be formed on the surface of the microcapsule walls. One way to ameliorate these problems is to extract the organic solvent with another solvent which is soluble in water and the organic solvent but does not dissolve the polymer (Gevaert, Photo-Production N. V., French Patent No. FR1362934). Another way to reduce the problems is to conduct a controlled evaporation of the solvent by gradual heating combined with pressure reduction.

In complex emulsion in-water drying, it is preferable that the organic solvent and the polymer not be miscible with the active ingredient, so it could be encapsulated. The active ingredient may be in aqueous solution or dispersion, or as solid powder. In an aqueous solution, if the dissolved active drug has a low molecular weight, it will tend to diffuse through the microcapsule wall during the encapsulation process. On the other hand, if it is a molecular substance with a molecular weight of several thousand Daltons, it will be retained inside the microcapsule.

The complex emulsion in-water drying method for encapsulation of highly hydrophilic pharmaceutical drugs is frequently used. Discontinuous procedures to obtain prolonged release microcapsules for injectable use, for implants, and transdermal or oral administration are described in, among others, European Patent No. EP0765659, and U.S. Pat. Nos. 4,652,441, 4,954,298, 5,271,945, 5,330,767, 5,611,971, and 5,651,990.

Discontinuous procedures for encapsulation of water soluble peptides for pharmaceutical uses, using this complex emulsion in-water drying method and PLGA or PLA as encapsulating polymers, show some drawbacks such as high dispersion of particles sizes that range from 1 to more than 400 microns, micro particles adhesion, process control difficulties, and poor reproducibility.

To prepare the first emulsion (W/O) in a discontinuous process requires variable intensity of agitation and mixing time that are dependent not only on the size of process, but also on other variables such as size and shape of the mixer. Because of the high viscosity of the phases, a good agitation or mixing of the total mass cannot be obtained. The shear forces applied by the mixing element (agitation turbines, dispersers, or ultrasound) can be transmitted only a few millimeters from the applying point. The result is a high dispersion of particle size in the first emulsion (W/O).

The preparation of the second emulsion, where the total external aqueous phase is placed in one reactor and the first emulsion (W/O) is added slowly to form the complex emulsion [(W/O)/W], is strongly dependent on factors such as: time in adding the phases, temperature, initial volume of first emulsion to second emulsion ratio, polymer concentration in the organic phase, nature and concentration of the protective colloid in the second aqueous phase, and position of the injection point of the (W/O) emulsion. Consequently, the control of this discontinuous process is extremely complicated. The results are high dispersion of particle size and low yields of microencapsulated material which passes through a mesh 200 (75 microns), the maximum size suitable for injectable preparations. It has been observed that traditional discontinuous manufacturing processes yield near to 30% of microcapsules having a diameter greater than 75 microns.

When the second emulsion is formed by adding the first emulsion over a total volume of the aqueous phase where the microcapsules will be formed, an important factor is the location of the first emulsion injection point. When the external aqueous phase is strongly agitated, particles of different sizes may be formed practically in the entire volume of the external aqueous phase. When these particles reach a size such that the surface evaporation of the volatile solvent allows the hardening of the microcapsule, this microcapsule can no longer reduce its size whatever be the length of the agitation time. The result is a wide dispersion in final particle size: microcapsules formed farther away from the point of application of shear forces are of a larger size whereas those formed in the neighborhood of the shear force application point are of a smaller size.

As it was mentioned previously, microcapsules consolidate when the superface evaporation of the volatile solvent used to dissolve the polymer hardens the surface to such an extent that is no longer possible the subdivision of microcapsules into smaller size particles. This evaporation is strongly dependent on the water ability to eliminate the organic solvent by absorption. For example, methylene chloride reaches a solubility of about 1.3% by weight at room temperature. In a discontinuous system this absorption capacity is time-dependent. At the beginning of the operation the microcapsules are formed in a medium where there is only water with a protective colloid with tensoactive activity. On the other hand, at the end of the mixing, the microcapsules are in a complex water-tensoactive agent system with increasing amounts of solvent and microcapsules. In this last situation, there is an increased probability of particle agglomeration.

Several of the procedures described in the literature include, after the separation of the external aqueous phase, the steps of washing the microcapsules with water followed by drying to remove moisture, milling and sieving of the dried product to eliminate particle agglomerates and homogenize its granulometry and, finally, the dosing of the solid to obtain the final product. These operations with solids present the same difficulties and demand the same care that are typical of operations with injectable pharmaceutical powders. Expensive equipment must be used to ensure sterile conditions, and prevent contamination and moisturizing of the microcapsules since the material is extremely hydrophilic, presents a high specific surface and must contain no more than 1% of water.

Further, in discontinuous methods, active peptide losses can reach up to 70% for the full process. These losses are calculated by comparing the amount of active peptide used as raw material and the amount retained in those microcapsules of suitable size to be used as an injectable product. The losses include the amount of active peptide that is entrapped in microcapsules larger than 75 microns, plus the amount that is dissolved in the non-emulsified medium, plus the amount lost during the washing step, plus the amount entrapped in very small microcapsules that also go away during washing.

SUMMARY OF THE INVENTION

This invention relates to a novel process for producing microcapsules for the sustained release, in adjustable release periods, of water soluble peptides. The process comprises the following steps: (1) continuously intermixing an aqueous solution of a water-soluble active peptide and a retention substance with an oily solution of a biodegradable polymer in an organic solvent that is insoluble or only slightly soluble in water, in a first mixer closed to the atmosphere to produce a first emulsion; (2) cooling the emulsion; (3) continuously intermixing the emulsion and an aqueous phase containing a protective hydrophilic colloid in a second mixer also closed to the atmosphere to produce a second emulsion; (4) removing the organic solvent from the second emulsion in a closed vessel to produce microcapsules containing the water soluble peptide; (5) adjusting the size distribution of the microcapsules; (6) dispersing the microcapsules in an aqueous medium containing a lyophilization excipient; (7) distributing the aqueous dispersion of microcapsules into vessels and freezing the medium at a temperature of less than about 20° C.; and (8) lyophilizing the frozen microcapsule dispersion.

The invention also relates to microcapsules produced according to the above described novel process. The invention also relates to the use of these microcapsules in the manufacture of formulations for the sustained release of materials.

The process of this invention reduces the number of operation steps of the process; improve the reproducibility of the process variables and, thus, facilitates the control of the process; produces a narrow and reproducible particle size distribution, composition and internal distribution of the active agent and, thus, facilitates the production of microcapsules with controlled release periods of the active drug; ensures a high retention of the active material inside the, microcapsules and, thus, minimizes losses of expensive raw materials; substantially improves the yield of particles with the desired size; minimize product exposure to the atmosphere during the process steps and, thus, decreases equipment requirements (and associated costs) to ensure sterile condition and low contamination; and improves the quality of the lyophilized product. Thus, the novel process substantially improves manufacturing productivity in comparison to existing processes and results in a product of higher quality.

Figure 1:
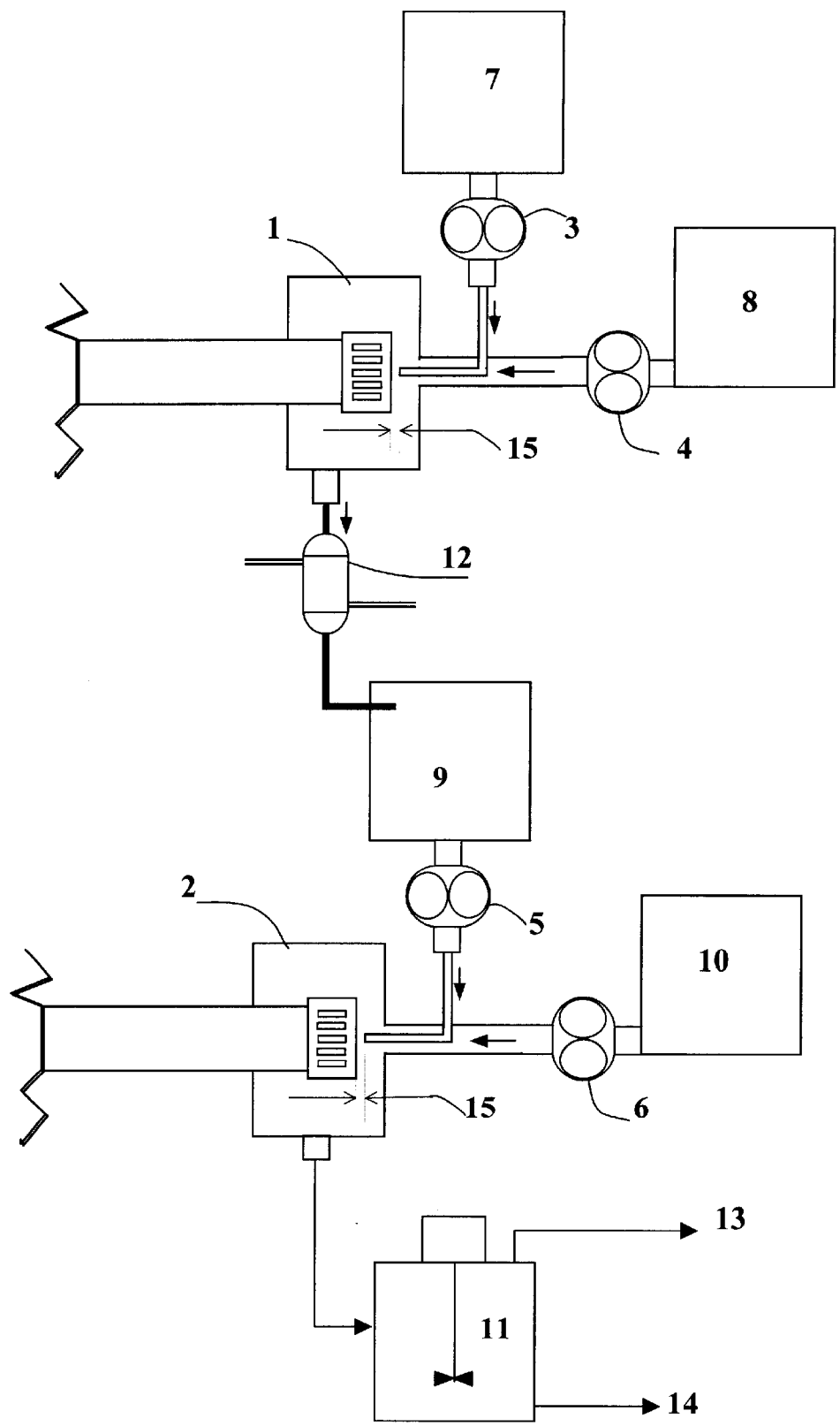
FIG. 1 represents a scheme of the first stages of the continuous process for microcapsules manufacturing References.

1: First intense agitation equipment or first mixer. The drawing shows a rotor-stator assembly as an example of the agitation device.

2: Second intensive agitation equipment or second mixer.

3: Active peptide aqueous solution dosing apparatus.

4: Dosing apparatus for the oily solution of biodegradable polymer in an organic solvent.

5: Dosing apparatus for the first water/oil emulsion.

6: Dosing apparatus for the aqueous solution containing a protective hydrophilic colloid.

7: Container for the active peptide aqueous solution.

8: Container for the biodegradable polymer oily solution in an organic solvent.

9: Container for cooling first emulsion.

10: Container for aqueous solution containing protective hydrophilic colloid.

11: Vacuum evaporator with agitator.

12: Cooler.

13: Vacuum line.

14: Finished microcapsules line that follows to centrifugation, washing process, fractionating, package, agitation freezing, and lyophilization.

15: Distance between the inside feed tube in the intense agitation equipments and the agitating element, which must not be greater than 20 mm.

Figure 2:
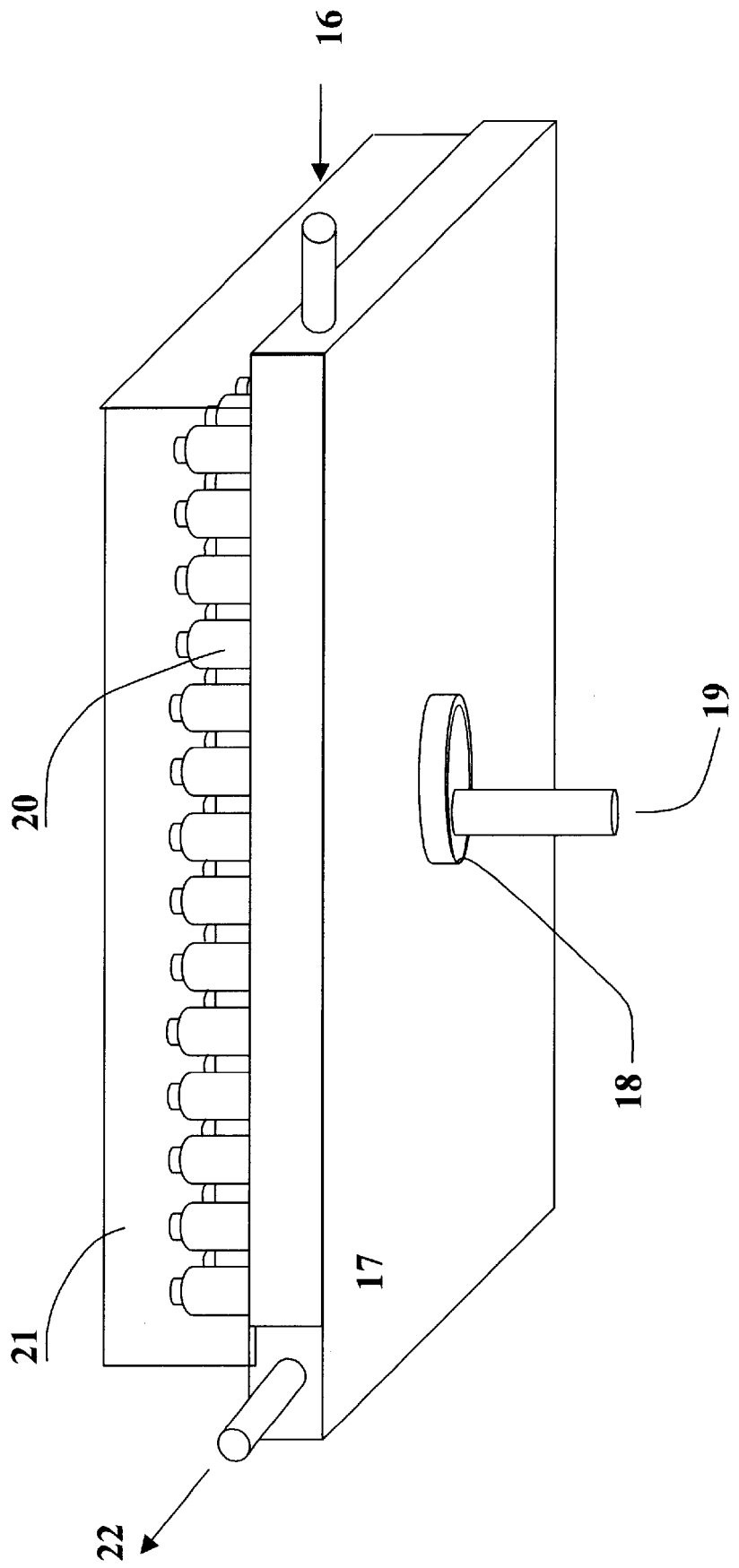

FIG. 2 represents a scheme of an orbital agitation freezing equipment

References:

16: Refrigerating liquid inlet.

17: Refrigerating plate where the refrigerating liquid circulates at very low temperatures.

18: Eccentric system that allows circular movement of the plate.

19: Eccentric axis that ties to electrical motor of adjustable speed.

20: Final packages containing the suspension of microcapsules.

21: Plate covering to prevent ambient moisture condensation and to keep the vessels closed to the atmosphere.

22: Refrigerating liquid outlet.

Figure 3:
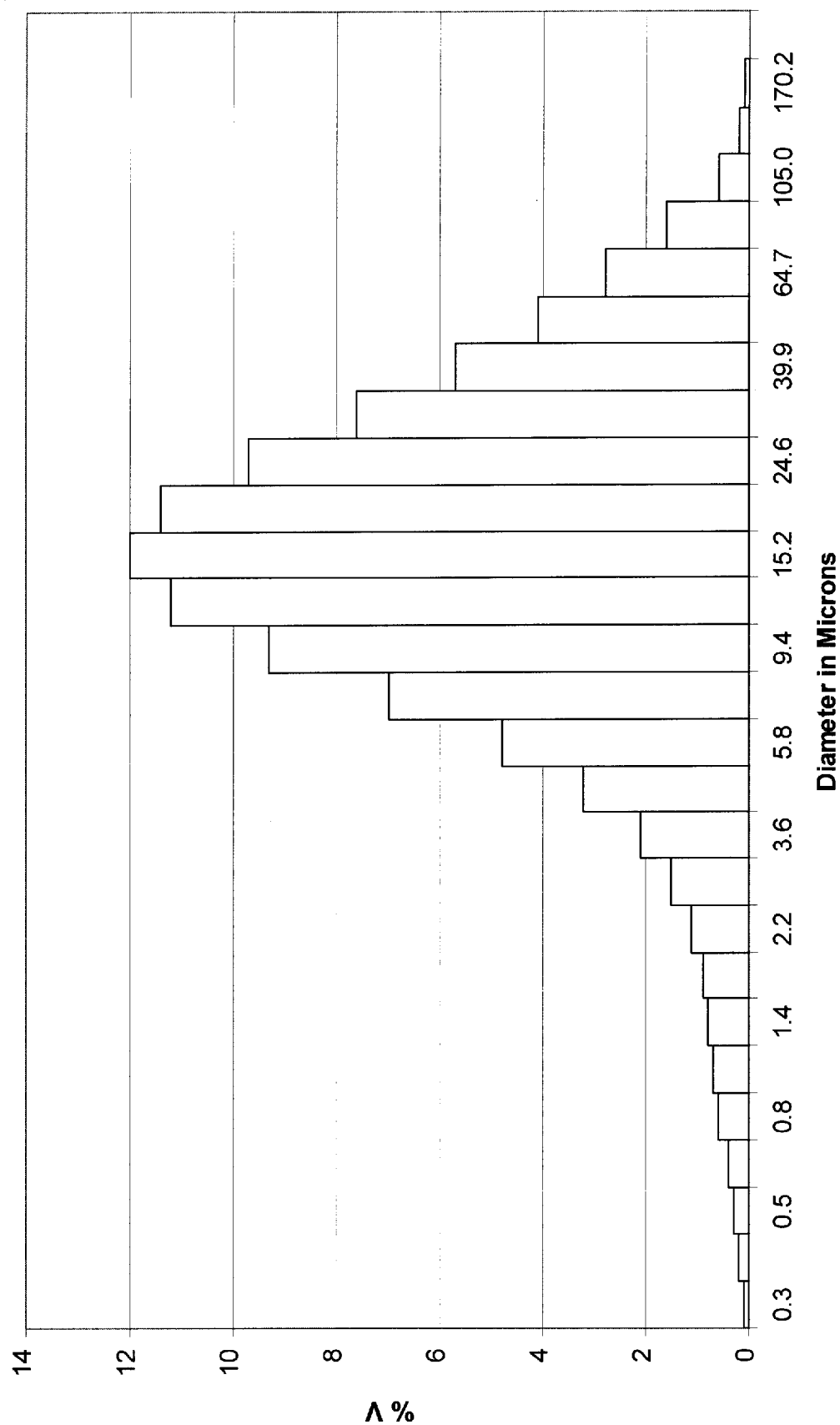

FIG. 3 is a graphic that represents the distribution of microcapsule diameter obtained in example number 1. (The figure shows the volumetric percentage of particles having diameter as indicated on the diameter axis (in microns). The particle diameter distribution was determined by laser interferometry. The average diameter was about 15 microns, and the fraction having diameter larger than 75 microns was less than 2.5%.)

Figure 4:
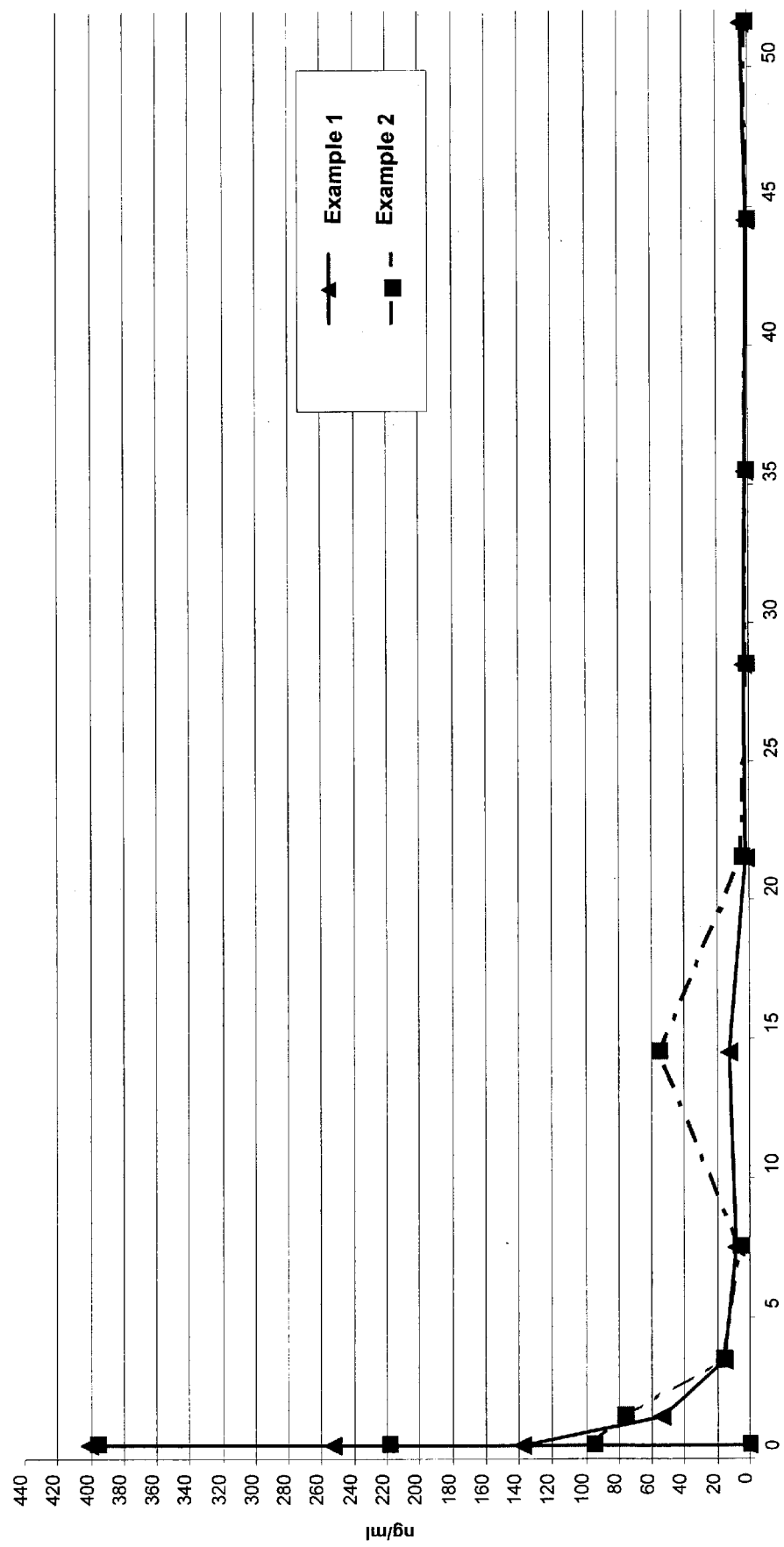

Microcapsules obtained in the process described in examples 1 and 2 were tested in vivo, to evaluate the release kinetic, of leuprolide acetate in Wistar rats. The test results are shown in FIG. 4. The horizontal axis shows days since inoculation, while the vertical axis indicates leuprolide acetate concentration in the blood, measured in nanograms per milliliter. The leuprolide acetate concentration was measured by Radioimmunoassay.

Figure 5:
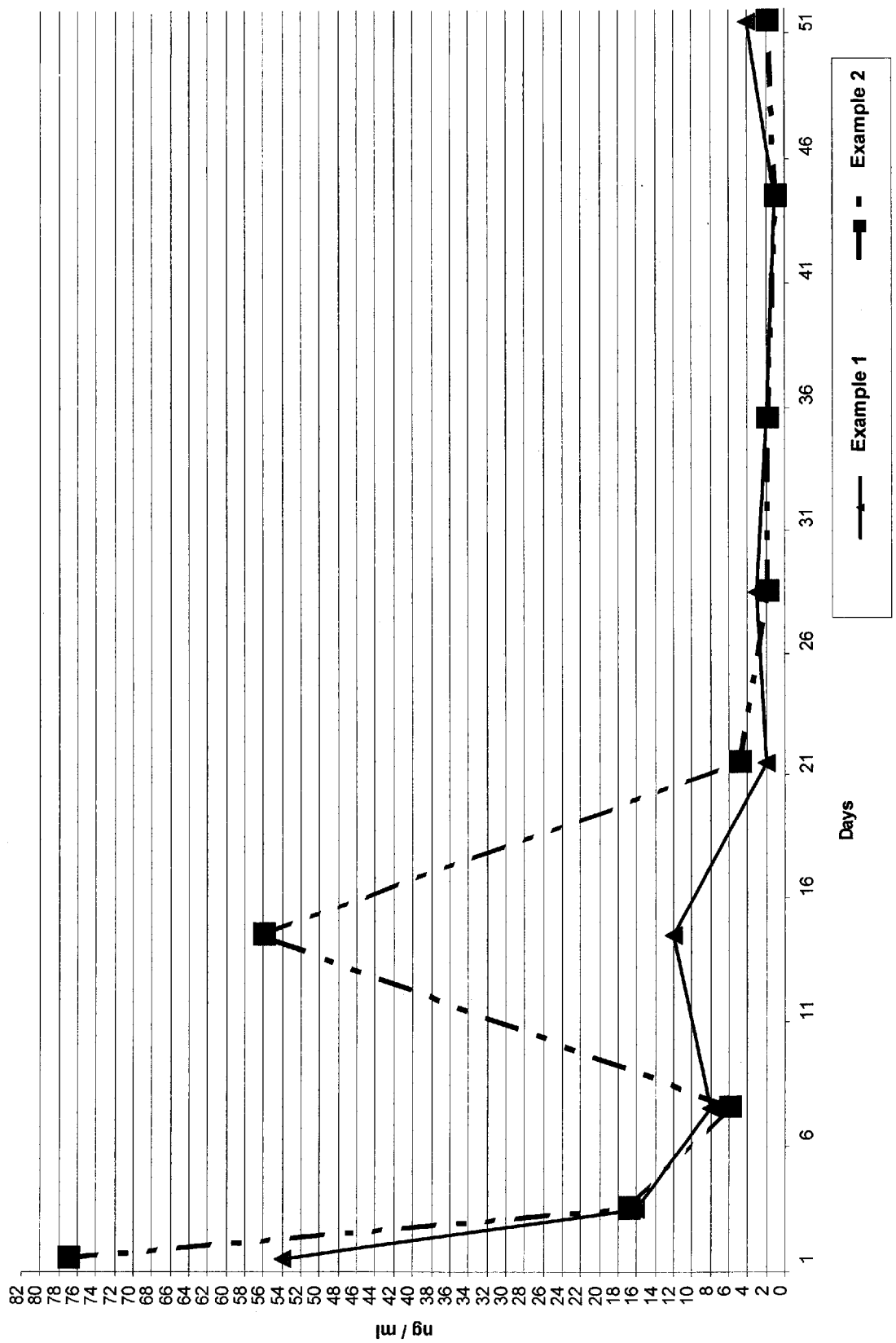

FIG. 5 is just an enlargement of FIG. 4.

DETAILED DESCRIPTION OF THE INVENTION

It has been discovered that many of the difficulties described above that are associated with existing methods for manufacturing microcapsules of pharmaceutical grade and that are based on the intermediate formation of a complex emulsion of the (W/O/W) type and use PLGA and PLA as encapsulating polymers are overcome by the process of this invention. This novel, continuous method to manufacture microcapsules uses, in sequence, two mixers that are capable of intense agitation of the mixture and closed to the atmosphere to obtain the intermediate complex emulsion. This emulsion continues being processed as a liquid suspension until its distribution into vessels, freezing under agitation and lyophilizing.

The invention is capable of different embodiments within the scope of the claims as it will be clear in the discussion that follows. In that discussion and the examples provided preferred embodiments of the invention are described. Other embodiments within the scope of the claims herein will be apparent to one skilled in the art from consideration of the specification or practice of the invention disclosed herein. It is intended that the specification, together with the examples be considered exemplary only, with the scope and spirit of the invention being indicated by the claims which follow the examples.

The advantages and characteristics of the present invention are better explained through the following detailed description, where numeric reference is made to each detail that can be observed in the drawings.

The first stage of a preferred embodiment of the process of the invention is the emulsifying of an aqueous solutions containing an active peptide and a retention substance into an oily solution of a biodegradable polymer dissolved in an organic solvent which is only slightly soluble in water. This emulsifying stage is carried out in a first mixer that is closed to the atmosphere and capable of imparting intense agitation to the mixture. The aqueous and the oily solutions are continuously fed to the mixer by dosing apparatuses. As the result of the agitation a water/oil emulsion is formed in and continuously withdrawn from the mixer. Thus, the mixer operates in a continuous manner. This first water/oil emulsion, after being cooled, is fed by another dosing apparatus to a second mixer also closed to the atmosphere and capable of intense agitation. The water/oil emulsion is then emulsified in this second mixer in a vehicle aqueous phase containing a hydrophilic protector colloid, which is also fed by a continuous dosing apparatus. A second complex emulsion of the water/oil/water type is formed in and continuously withdrawn from the second mixer. Thus, this second mixer also operates in a continuous manner. The complex water/oil/water emulsion is then continuously fed to a closed vessel where the solvent is evaporated by pressure reduction, and the microcapsules consolidate. The micropcasules are then subject to wet operations to remove impurities and adjust their particle size distribution to that suitable for final use. These operations are: microcapsule suspension sieving and centrifuging, washing with water, dispersion into a medium containing a lyophilizing excipient, distribution into suitable containers, freezing in an orbital agitation freezer at temperatures below −20° C., and lyophilizing in the same distribution containers. Details of this process follow.

The substances subject to microencapsulation by the process of the present invention are water soluble, active peptides containing between 5 and 20 aminoacids. Representative examples of these active peptides are: leuprolide, goserelin, nafarelina, triptorelin and buserelin acetates. The dosage recommended for these substances indicate that the microcapsules containing them should be administered to patients for periods between 1 and 18 weeks.

To produce the microencapsulation of these substances by the method of the present invention, it should be prepared first an aqueous solution of one of the above named active peptides in concentrations that may range from 5% to 60% by weight, or more preferable between 10% and 40% by weight of the aqueous phase. Depending on the peptide to be encapsulated, an active peptide retention substance can also be dissolved in this aqueous solution, at a concentration ranging from 0% to 10% by weight, and preferentially, between 0% and 7.5%. This active peptide retention substance must also have the property of giving a semisolid consistence to the aqueous phase, possibly by external actions such as refrigeration. Among the retention substances that can adjust the active peptide release, after intensive laboratory testing indicated the advantage of using gelatin of 70 to 100 Blooms, type B, of bovine origin. The indicated gelatin gives a good response in retaining the active peptide inside the aqueous phase, without hardening excessively this phase. It was verified that gelatins with other characteristics cause the emulsion process to be poor regarding the final retention of active peptide in the microcapsules. In certain cases, depending on the active peptide and the desired release period, it may not be necessary to incorporate a retention substance. The temperature of the prepared aqueous solution is raised to values between 40 and 65° C. to ensure dissolution.

At the same time, a biodegradable and biocompatible polymer is dissolved in an organic solvent that has very low or almost no mutual solubility with water. For the purposes of the present invention, the maximum solubility limit of the organic solvent in water was adopted as not greater than 6% by weight in relation to water. The polymer must also be slightly soluble or insoluble in water. In this manner an homogeneous oily phase of the polymer the organic solvent was obtained. At the end of the process of the present invention, the polymer becomes the constituent of the microcapsule matrix.

Without neglecting other polymers mentioned in the related art, among the polymers that can be used in the process of the present invention, the homopolymer of (d,l)-lactic acid (PLA) and the copolymers of (d,l)-lactic and glycolic acids (PLGA) are preferred. These polymers are soluble in chloroalkanes such as methylene chloride; dichloroethane; chloroform and carbon tetrachloride, or ethyl ether; benzene; methyl acetate; ethyl acetate and mixtures of them. Alkanes of low molecular weight can be added to these mixtures. Methylene chloride is preferred organic solvent in the present invention for its ability to dissolve the polymers PLA and PLGA, its easy evaporation in the presence of an aqueous phase due to its high vapor pressure, and its bactericide action that facilitates the aseptic pharmaceutical process, allowing for the sterilization of the polymer by a chemical agent. Other polymer sterilization methods such as ionizing radiation, wet heat, dry heat or filtration through a 0.2 micron membrane are not recommended in this application.

The molecular weight of the polymer affects some product characteristics such as release rate, biodegradation time profile and particle size distribution. High molecular weight values are associated with higher viscosity values, and thus, with the formation of larger particles and longer peptide release periods.

The average molecular weight of the biodegradable polymer is selected, for the purposes of this invention, in the preferred range of between 10000 and 30000 Daltons, being the most desirable range between 12000 and 25000 Daltons. A specially suitable polymer to produce microcapsules with long release period is the polylactic acid (PLA) with a molecular weight between 10000 and 25000 Daltons. If a copolymer of (d,l)-lactic and glycolic acids (PLGA) is used the mole ratio of monomers Lactic:Glycolic may be between 100:0 and 50:50.

The polymer concentration in the organic phase is regulated between 10% and 60% by weight; more preferrably between 25% and 45%, being this concentration an important factor in the degree of dispersion to be obtained in the subsequent emulsion of the aqueous phase. Fixing temperature and polymer concentration, the viscosity of organic phase is also fixed.

The active peptide aqueous solution and the biodegradable polymer oily solution are subject to mixing and intensive agitation process to obtain a first water/oil emulsion. This operation is one of the most critical stages to obtain a dispersion of the aqueous phase particles into the oily phase. To this effect, a continuous procedure is used, which allows for the formation of the emulsion under reproducible and suitable conditions. As a possible embodiment of the present invention, the homogenizing device is a first mixer or intense agitation chamber, closed to the atmosphere, of cylindrical shape, and which uses a rotor-stator assembly as mixing or agitating element. The purpose of this closed chamber is to obtain an agitation intensity enough to achieve the required degree of dispersion of the aqueous phase that contains the active peptide in the oily phase.

Regarding the fluid dynamic conditions necessary to produce and maintain this first water/oil emulsion, it has been established that with a 17.5 millimeter diameter rotor, rotating against a fixed grooved stator in the rotor-stator assembly, the rotor speed must be between 5000 and 12000 rpm for a total flow rate of the two phases between 30 and 500 ml per minute, to obtain a good degree of dispersion and to ensure emulsion stability for the subsequent formation of the second emulsion. Moreover, the rotor speed is controlled independently from the other process variables, which allows a regulation adjusted to the desired process conditions. With the results obtained in the type of homogenizing device described above, it was established that this first water/oil emulsion must be formed at residence times less than 7 seconds and with rotor peripheral speeds between 3 m/sec and 12 m/sec. Residence time is the time that the phases stay in the intensive agitation equipment, whichever type of agitation element is employed.

The scale of this first water/oil emulsion may be reduced or increased by changing the agitation chamber and the rotor-stator assembly, until the desired degree of dispersion is obtained.

When the experiments are conducted at laboratory or pilot plant scale, this first water/oil emulsion may be formed using as homogenizing device a closed agitation equipment or mixer comprising a sonic mixing probe on sonotrode, which will form the emulsion by ultrasound. This equipment can be scaled up to higher production rates.

An alternative version of this invention, specifically suitable for small scale production is to form the first water/oil emulsion in an intense agitation chamber with continuous flow of the aqueous and oily phases, the chamber containing a sonotrode as the agitation element, operating at frequencies between 20000 and 50000 Hertz and power of not less than 30 watt.

Another variable controlling the dispersability of the aqueous phase in the oily medium of this first emulsion is the mass ratio of the phases that enter to the intense agitation equipment. From experiments made, it can be concluded that is convenient to operate with an oily phase/aqueous phase mass ratio between 3 and 20, preferably between 6 and 10. To control the dispersability of the aqueous phase in this first emulsion it is also important to maintain the temperature in the intense agitation equipment between 10° C. to 35° C.

In the process of this invention, the water/oil emulsion produced in the first intense agitation equipment is continuously refrigerated in a conventional heat exchanger, and transported to a closed intermediate container. The purpose of this cooling is to stabilize this first dispersion to induce the aqueous phase gel formation by increasing its viscosity. The temperature values that this first emulsion must reach are between 5° C. and 25° C., more preferably between 10° C. and 20° C.

The next stage in the manufacturing process is the production of a second emulsion, where a first component is the first emulsion constituted by the aqueous phase containing the active peptide, micro-emulsified into the oily phase composed by the polymer solution in an organic solvent; and the second component is a vehicle aqueous phase, an aqueous solution of a hydrophilic protective colloid with tensoactive activity, which is prepared for this purpose. Polyvinyl alcohol (PVA) is adopted as the protective colloid. The result of this operation will be the formation of a complex emulsion water/oil/water from which the microcapsules containing the active peptide can be formed.

Several parameters have influence on the preparation of this second emulsion. In this sense, the chemical composition of the vehicle aqueous phase, the mass proportion of the same with respect to the first emulsion, the temperature and the agitation regime are essential variables which may be controlled to obtain a microcapsule population with a size range such that a large mass fraction of the particles is between 1 and 75 microns.

In a preferred form of the present invention, the vehicle aqueous phase is prepared by adding to the water, as hydrophilic protective colloid, polyvinyl alcohol (PVA) of an apparent viscosity of 25 to 50 centipoises, measured in a 4% by weight aqueous solution and temperature of 20° C.; with a degree of hydrolysis between 85% and 89% and concentration between 0.1% and 1% by weight, preferably between 0.2% and 0.4%. The presence of polyvinyl alcohol (PVA), as a hydrophilic protective colloid and, simultaneously, as tensoactive agent, ensures the stability and low particle aggregation, which allows positive results in microcapsule formation. The optimal temperature to produce this second emulsion is between 10° C. and 30° C., more preferably between 12° C. and 20° C.

To produce this second complex water/oil/water emulsion it is used as a homogenizing device, a intense agitation equipment closed to the atmosphere, of cylindrical shape, and using as agitation element an rotor-stator assembly with grooves. The first emulsion and the vehicle aqueous phase arrive to this intense agitation equipment by two different dosing pumps.

Referring to the agitation conditions, it is convenient to make this second emulsion by operating the rotor at high speed. For a 17,5 mm of diameter rotor, rotating against a stator with grooves, it has been concluded, after a number of tests, that the rotor angular speed may range between 10000 and 25000 rpm, preferably between 14000 and 18000 rpm, for a total inlet flow rate of the first emulsion plus the vehicle aqueous phase between 500 and 10000 ml/min. These angular speeds of the rotor can be expressed in a more general way taking into account the possibility of scaling-up the process in terms of rotor peripheral speed, which must be higher than 9 m/sec. to obtain the desired results. Moreover, the rotating speed of the rotor is controlled independently from the other variables of the process, which allows precise regulation of the desired process conditions. In addition, the residence time of the phases in this second intense agitation equipment, to form the second water/oil/water emulsion, must be less than 1 second.

In order to complete the description of set of conditions to be met to prepare this second emulsion by the method of the present invention, the mass ratio between the vehicle aqueous phase and the first emulsion must be between 30 and 80; more preferably between 35 and 55. The temperature to make this water/oil/water emulsion must be controlled between 10° C. and 30° C.

The procedure consists in adding the first micro emulsion containing the active peptide, in a continuous fashion, to a continuous flow of the aqueous phase containing the tensoactive agent. The phases are mixed rapidly in the agitation equipment by applying large shear forces with the rotor-stator assembly to induce microcapsule formation. These microcapsules, in close contact with the aqueous phase, lose the superficial methylene chloride coverage and are transformed from a water/oil/water emulsion into microcapsules sufficiently rigid to be able to stay in suspension without producing aggregates, and with a particle size distribution that, once the temperature and the mass proportion of the components in both phases are fixed, is determined by the rotor speed. From this rotor-stator assembly, which also acts as a centrifugal pump, the complex emulsion is sent to an evaporation vessel where, by gradually decreasing the pressure until values between 30 and 80 Torr, more preferably between 40 and 60 Torr, most of methylene chloride is removed which causes the hardening of the microcapsules that, under those conditions become so rigid that they are able to withstand centrifugation without agglomerating.

FIG. 1 illustrates some technical details concerning the scope of this invention which are described next. The closed container (7) contains the active peptide aqueous solution, while (8) is the container for the polymer solution in an organic solvent. Two dosing pumps, (3) for the aqueous phase and (4) for the oily phase, cause a constant and controlled flow of the two phases that are injected inside the intense agitation equipment (1), where the first water/oil emulsion is produced. A detail that stands out as a part of this invention is that the aqueous phase enters into the agitation equipment by a central tube which ends at a distance not greater than 20 mm, or more preferably not greater than 10 mm, while the oily phase enters by an external coaxial conduct. Both feed entrances reach the intense agitation equipment in front of the agitation element.

The dosing pumps (3), (4), (5), and (6) are independently adjustable flow pumps, having their own control devices and, in general, are of low flow rates. In the context of the present invention, and depending on the scale of production, pumps (3) and (4) may be adjustable speed gear pumps, or stainless steel piston pumps where the piston is moved by a worm screw connected to a completely variable ratio speed reductor with a synchronic or controlled speed motor.

From the intense agitation equipment (1), that operates completely closed, the first water/oil emulsion passes through a heat exchanger (12) where it is cooled at a preestablished temperature, and it is discharged into closed vessel (9) which functions as feeder of that emulsion to form the second emulsion. Vessel (10) acts as a closed place to prepare and contain the vehicle aqueous phase with the hydrophilic protective colloid dissolved. From these containers the first emulsion, by pump (5), and the vehicle aqueous phase, by pump (6), are fed continuously into the intense agitation equipment (2) where the second water/oil/water emulsion is produced.

As in the case of the first intensive agitation equipment, the location of the injection point of the first emulsion and the vehicle aqueous phase, as well as the distance between that injection point and the rotor, are very important factors in the successful manufacturing of the second emulsion process. In the scope of this invention, it is established that is convenient to introduce the first water/oil emulsion by a central tube, and the vehicle aqueous phase by a coaxial annular tube, and that the central tube ends in front of the rotor (2), at a distance preferably greater than 20 mm.

The dosing pump (5), depending on the process scale, may be a controlled speed gear pump, or a stainless steel piston pump where the piston is moved by a worm screw connected to a variable ratio speed reducer with a synchronic or controlled speed motor. Pump (6) may be, among other alternatives, an adjustable peristaltic pump which, in the context of the present invention, must have a flow greater than 400 ml/min.

The second water/oil/water emulsion with the active peptide microcapsules already partially formed is transferred by the action of the agitator pumping (2) to a closed vessel (11) that has the following elements: a low speed marine type agitator, preferably of not more than 150 rpm, or a magnetic agitator, a thermostat to keep the temperature between 10° C. and 40° C., a connection with an automatic valve to an adjustable vacuum system (13), and a closed discharge conduct, with valve, to discharge the aqueous phase with the micro particles in suspension to a closed sieving equipment. In this vessel (11), the final evaporation of the organic solvent and the final microcapsule consolidation take place to prevent the possible foam formation during the organic solvent evaporation process, this vessel must not be filled with liquid over 60% of its total volume.

The microcapsules in suspension are sieved through a 200 mesh that allows particles sizes smaller than 75 microns to pass through. The material lost in particles larger than 75 microns is less than 10% and, generally, less than 5%, a very small value when compared with the results in discontinuous reactors where the addition of the first emulsion to the aqueous phase is made without caring about the location of the point of injection, and where the losses in discarded materials larger than 75 microns of size can rise to more than 30%.

The suspension is now centrifuged into a continuous equipment where large size microcapsules are precipitated and gathered after being washed with distilled water to remove any protective colloid and peptide residues. The losses in this case are strongly related to the percentage of peptide trapped in the microcapsules, which generally is between 80% and 90%. Small size microcapsules and thinly divided polymer can be eliminated by adjusting the centrifuge speed and the suspension flow. Then, this separation process is preferred to filtration which does not remove small size particles that can increase the initial release, or "burst effect" of the final product. In this way, the active peptide losses during the whole process, respect to the quantity used as raw material, is less than 30%.

Once the washing is finished, the microcapsules are removed from the centrifuge, resuspended in distilled water, and discharged into a temporary holding vessel. The microcapsules are maintained in this inert aqueous medium that is homogenized by agitation and the amount of active peptide present is evaluated by HPLC. The next step is to add the necessary quantity of an aqueous solution of a lyophilization excipient that facilitates the later stages of lyophilizing and final drying. The excipient may be lactose, polyvinylpyrrolidone, etc. For this purpose, mannitol use has been found appropriated, in concentrations between 0.5% and 2%, preferably between 0.8% and 1.5% by weight referring to the total suspension.

The microcapsules aqueous suspension is aseptically fractionated into suitable containers. This step of the process is conducted in closed system and maintaining the agitation of the aqueous medium that contains the microcapsule, to ensure the suspension homogeneity.

The containers receiving the fractionated suspension may be small dose vials which after lyophilization, are sealed to obtain the final product already packaged for consumption, or larger size containers that, after lyophilization, allow to obtain the product in bulk as dried powder.

Under these conditions, the operation of freezing the vessel contents is carried out in an orbital agitation freezer device, designed to place the vessels containing the suspension over a tray where a circular motion is produced. The tray support base is a refrigerating plate that by circulation of the refrigerant fluid may be cooled to temperatures between −20° C. and −80° C., or preferably to temperatures between −30° C. and −60° C. By this device and method, developed as a part of the present invention, the microcapsule suspension is frozen and, thus, reducing particle deposition on the bottom of each vial. This procedure enormously facilitates the microcapsule lyophilization and final drying, producing a lyophilized material of greater homogeneity that improves considerably the reconstitution of the microcapsules suspension, making this reconstitution instantaneous, prevent the microcapsule agglomeration in time, and improves their pharmaceutical stability. The device is shown in FIG. 2 of the present document. In a preferred embodiment of the present invention, the freezing process with orbital agitation is made gradually from a temperature of 15° C. to a final temperature −30° C., during a total estimated time between 10 min. and 60 min, or more preferably between 15 and 30 min.

FIG. 2 shows the orbital agitation freezer for the already fractionated suspension of micro-particles. The stainless steel plate (17) is supported by springs attached to a fixed structure that does not appear in the Figure. The refrigerating fluid circulated inside the plate is connected by inlet tubes (16) and outlet tubes (22) which are connected by hoses to a programmed-refrigeration external equipment which sends the refrigerating fluid to the plate. The flasks containing the microcapsules suspension in their final dosage are put over the plate and covered with a sterilized polycarbonate box (21). The eccentric system (18) is in the plate (17) and it is connected to a adjustable speed motor by the axis (19). For purposes of the present invention, the eccentric disc (18) is made so that the orbital movement of the platform presents a rotating radius smaller than the bottom radius of the containers placed on the tray and the motor speed is adjusted, according to each case, between 20 and 50 rpm. In the case that the containers are not cylindrical, the above mentioned radius of the container is understood to mean the radius of the circle in which the container base is circumscribed.

The next step is the microcapsule lyophilizing in the same container where the microcapsule suspension was fractionated. The lyophilizing procedure is standard. The product must not be warmed up above the softening temperature of the polymer used. As the final stage of the continuous process of the present invention, the vials are closed in a nitrogen atmosphere inside the lyophilizer.

To obtain the manufacturing of a specified quantity of microcapsules, this continuous process is conducted for a corresponding time period, during which, the microcapsules maintain practically the same size, the same particle diameter dispersion, and the same active peptide concentration, from the beginning to the end of the operation.

EXAMPLE 1

Active Peptide Microencapsulation with Rotor-stator Type Agitator

The pharmaceutical raw materials used meet the quality requirements of the pharmacopoeia. The process is conducted under aseptic conditions, and under laminar flow class 100. 14.5 g of leuprolide acetate with a purity grade greater than 99%, with 2.29 g of gelatin, type B, 75 Blooms from bovine origin, are aseptically lyophilized. The lyophilized gelatin and the leuprolide are dissolved into 26 ml of water, warmed up to dissolve at 60° C. are taken to a dosing vessel (7). In addition, 334 g of a PLGA in methylene chloride solution (this solution is prepared with 130 g of PLGA 75:25, MW: 14000 D. analyzed by gel permeation chromatography with polystyrene standards and 162 ml of methylene chloride) is put into the dosing vessel (8). They are dosed by their respective dosing pumps, of the piston with worm screw type, being 250 ml/min the total inlet flow rate to the first intense agitation equipment, and being 7.8 the mass ratio of the oily polymer phase to the aqueous peptide phase. The continuous agitation equipment contains a rotor-stator assembly (IKA), where the peripheral rotor speed is 5 m/s. This first emulsion is refrigerated at 20° C. when it passes through refrigerator (12) going to container (9) where it is accumulated until the necessary quantity for the process is obtained. The total inlet flow rate to the second intense agitation equipment is 2330 ml/min. The mass ratio of the vehicle aqueous phase to the first water/oil emulsion is 67. The first emulsion is propelled by a dosing pump (5) of the piston with worm screw type into a stream of water with 0.25% of polyvinyl alcohol of apparent viscosity of 35 centipoises measured in aqueous solution, 4% in by weight, and temperature of 20° C., with a degree of hydrolysis of 85%, supplied from container (10) by a dosing pump (6), which, in this example, is of the peristaltic type, "Master-flex". This second agitation continuous equipment is a rotor-stator assembly (IKA), and the peripheral rotor speed is 15 m/s. From there the water/oil emulsion is transported to a vessel with magnetic agitation where the methylene chloride is evaporated by decreasing pressure during 90 minutes, reaching a pressure of 50 mm Hg in 45 minutes. The suspension so obtained is passed through a mesh 200 sift where 12.8 g (3.4%) of agglomerated microcapsules and these larger than 75 microns were retained. The suspension is then transported to a standard rotor of a continuous settling centrifuge (Beckman AVANTI J-25) by a dosing pump, at a flow rate of 240 ml/m, with a rotation speed of 3000 rpm. It is washed with 1000 ml of distilled water, the rotor is emptied, and the microcapsules are taken to a retention and dosage agitated recipient with a volume of 1750 ml, from where an approximately 1 ml sample is extracted to analyze the microparticles by HPLC. This analysis showed a content of 5.60 mg of leuprolide acetate/ml which implies a dosage of 1.34 ml, to obtain doses of 7.5 mg after adding 123.2 ml of an sterile 15% weight/volume solution of mannitol. In each vial 1.34 ml are dosed, and 1380 vials were obtained from the theoretical amount of 1886 doses, according to the consumed leuprolide acetate quantity. So, the leuprolide acetate loss during the complete process, respect to the used quantity as raw material, is 26.8%. These vials are placed in a lyophilizing tray, which is then put on the plate that is gradually refrigerated until a temperature of −50° C. is reached, while the eccentric orbital agitator moves at an orbital rotation speed of 120 rpm for 30 minutes. After this operation if finished, the tray is put into the lyophilizer and it is lyophilized until a pressure lesser than 10 microns, refrigerating at −40° C. during 6 hours; at −5° C. during 10 hours; at 0° C. during 10 hours, and at 25° C. during 4 hours, to obtain a degree of residual humidity less than 1%, and a methylene chloride contents less than 33 ppm. The vacuum is broken with sterile nitrogen and the vials are closed inside the lyophilization equipment. The lyophilized product is sealed and stored at room temperature and protected from light, for its later analysis.

The microcapsules obtained in this example were analyzed to determine their particle diameter distribution by laser interferometry analysis and the results are shown in FIG. 3. The average diameter was 15 microns and the fraction of the particles with a diameter larger than 75 microns was less than 2.5%.

Also, in vivo test were conducted, where the leuprolide acetate release kinetics was evaluated, in Wistar rats by RIA analysis, with a leuprolide antibody developed by the technique described in "I Yamazaki and H. Okada, Endocrinol. Jpn., 27 (1980) 593–605". A release profile like the one shown in FIG. 4 was obtained, and in an enlarged scale it is shown in FIG. 5.

EXAMPLE 2

Active Peptide Microencapsulation with Sonotrode Type Agitator in Water/oil Emulsion; and Rotor-stator in Water/oil/water Emulsion 1.84 g of leuprolide acetate with 327 mg of gelatin, type B,75 Blooms, of bovine origin, are aseptically lyophilized. The lyophilized gelatin with the leuprolide are dissolved in 3.3 ml of water, warmed up to 60° C. to ensure dissolution, and taken to container (7). In addition, 43.47 g of PLGA in a methylene chloride solution (this solution is prepared with 17.36 g of PLGA 75:25, MW: 14000 D. and 21.7 ml of methylene chloride) is placed in container (8). Both solutions must pass simultaneously, by two dosage pumps piston with worm screw type, at a 35 ml/min through the continuous equipment (Dr Hielscher Gmbh) thermostatised at 18° C., and agitated with a 2 mm sonic mixing probe at a power of 40 W, at 30 KHz (Ultrasonic processor UP 50 H, Dr. Hielscher Gmbh). The resulting water/oil emulsion is refrigerated to 20° C. and arrives to container (9). Then, it is injected with a dosing pump, piston with worm screw type, along with a flow of water with polyvinyl alcohol, 0.25%, that is incorporated from container (10) by a dosing pump, peristaltic type, Masterflex. These flows enter coaxially to the second intense agitation equipment that has an rotor-stator assembly (IKA). The peripheral rotor speed is 15 m/sec. The entering flow to this equipment is 2330 ml/m. The water/oil/water emulsion so obtained is continuously transported to container (11) that is provided with magnetic agitation and where the methylene chloride is evaporated in 90 minutes, reaching a pressure of 50 mmHg in 45 minutes. This suspension passes through a mesh 200 sieve, where 1.9 g (3.9%) of agglomerated microcapsules and those greater than 75 microns, are retained. The suspension is then conducted by a dosage pump, at a 240 ml/min. flow, to a continuous centrifuge (Beckman AVANTI J-25) that works at a rotation speed of 3000 rpm. There it is washed with a volume of 1000 ml of distilled water, the rotor is emptied, and the microcapsules are carried to a dosage machine with a volume of 255 ml, from where, a sample of approximately 1 ml is taken, to analyze the content of leuprolide acetate by HPLC, as a result a content of 5.62 mg of leuprolide acetate per ml is obtained. Resulting in a dosage of 1.42 ml to obtain 7.5 mg doses after adding 16.8 ml of a Mannitol solution 15% w/v. In final vials, 1.42 g are dosed and 185 dosed samples are obtained, from the theoretical 245, according the leuprolide quantity used. So, the loss of leuprolide acetate during the complete process, with respect to the quantity used as raw material, is 23.2.%. The vials containing the microcapsules suspension are put into the orbital agitation freezer at 20 rpm and are refrigerated gradually until −50° C. in a time interval of 25 minutes; then, it is lyophilized following the same sequence that in example 1, to obtain a humidity grade lesser than 1% and a methylene chloride content lesser than 33 ppm. The vacuum is broken with sterile nitrogen and the vials are closed inside the lyophilizer. The lyophilized product is sealed, and stored at room temperature and protected from light, for its later analysis.

EXAMPLE 3

Active Peptide Microencapsulation with Rotor-stator Type Agitator 17.83 g of goserelin acetate with 2.89 g of gelatin, type B, 75 Blooms from bovine origin, are aseptically lyophilized, and then both substances are dissolved in 32 ml of water, warmed up to 60° C. to ensure dissolution, and they are taken to the dosing vessel (7). On the other side, 332 g of a PLA of MW 20000 in methylene chloride solution (this solution is prepared with 154 g of PLA and 192 ml of methylene chloride) is put in the dosing vessel (8). They are dosed by their respective dosage pumps with a total flow of 100 ml/min, and a ratio of oily and aqueous phases of 6, to the first intensive agitation equipment, like in example 1. The resulting emulsion is cooled to 20° C. by passing through refrigerator (12), then to the recipient (9), and then injected into a flow of water with 0.25% polyvinyl alcohol. The total inlet flow to the second intense agitation equipment is 2730 ml/min, using a peristaltic pump, Watson-Marlow, for dosing. The second emulsion was made in a continuous equipment (IKA) with the homogenizer (IKA) at a peripheral speed of 15 m/s, and conducted to a magnetic agitation reactor in which the methylene chloride is evaporated by decreasing the pressure for 1 and a half hour, reaching a pressure of 50 mmHg in 45 minutes. The suspension so obtained is passed through a 200 mesh sieve, where 12.8 g (3.3%) of agglomerated microspheres, and those greater than 75 microns, are retained. The suspension is then conducted to a standard rotor from a continuous centrifuge (Beckman AVANTI J-25) by a dosing pump at a flow of 240 ml/m, with a rotation speed of 3000 rpm. It is washed with 1000 ml of distilled water, the rotor is emptied, the microcapsules are suspended in 3500 ml of water, from where a 1 ml sample is taken to be analyzed by HPLC. Results showed a content of 3.75 mg of goserelin acetate/ml, which implies a dosage of 1.00 ml to obtain doses of 3.6 mg after adding 160.4 ml of a 15% w/v mannitol solution. 1 ml is dosed into each vial, and 3652 dosed samples were obtained from the theoretical 4952, according to the used quantity of goserelin (73.7%). The vials were put on the plate and refrigerated at −50° C., with its tray for lyophilization over the circular agitator that moves at a speed of 120 cycles/minute, during a time of 30 minutes. Then the tray is put into the lyophilizer and it is lyophilized following the same sequence of example 1, to obtain a humidity residual of less than 1%, and a content of methylene chloride less than 33 ppm. The vacuum is broken with sterile nitrogen, and the vials are closed into the lyophilizer. The lyophilized product is sealed, and stored at room temperature and outside light, for its later analysis.

What is claimed is:

1. A process for producing microcapsules for the sustained release of water soluble peptides, the microcapsules having an adjustable release period, the process comprising the steps of:

continuously intermixing an aqueous solution comprising a water-soluble active peptide and a retention substance with an oily solution comprising a biodegradable polymer in an organic solvent that is insoluble or only slightly soluble in water, in a first mixer that is closed to the atmosphere to produce a first emulsion;

cooling said first emulsion;

continuously intermixing said first emulsion and an aqueous phase containing a protective hydrophilic colloid in a second mixer that is closed to the atmosphere to produce a second emulsion;

removing the organic solvent from the second emulsion in a closed vessel, thereby producing microcapsules of distributed sizes, the microcapsules containing the water soluble peptide;

adjusting the size distribution of the microcapsules;

dispersing the microcapsules in an aqueous medium containing a lyophilization excipient;

distributing the aqueous dispersion of microcapsules into a plurality of vessels and freezing the medium at a temperature of less than about −20° C.; and lyophilizing the frozen microcapsule dispersion.

2. The process for producing sustained release microcapsules according to claim 1, wherein the microcapsules have a particle size distribution ranging from 0.5 to 100 microns, with less than 10% of the microcapsules having a particle size greater than 75 microns.

3. The process for producing sustained release microcapsules according to claim 1, wherein the step of adjusting the size distribution of the microcapsules comprises the steps of sieving, centrifuging, and washing.

4. The process for producing sustained release according to claim 1, wherein the step of removing the solvent from the second emulsion is pressure reduction.

5. The process for producing sustained release microcapsules according to claim 1, wherein the active peptide aqueous solution and the biodegradable polymer organic solution are intermixed in a first mixer and are fed into the first mixer by a first set of dosing apparatuses, and wherein the first emulsion the aqueous solution containing the protective hydrophilic colloid are fed into the second mixer by a second set of dosing apparatuses.

6. The process for producing sustained release microcapsules according to claim 5, wherein the first set of dosing apparatuses are adjustable flow pumps.

7. The process for producing sustained release microcapsules according to claim 1, wherein the first emulsion and the aqueous phase containing a protective hydrophilic colloid are intermixed in a second mixer having a second set of dosing apparatuses, wherein the second set of dosing apparatuses are adjustable flow pumps.

8. The process for producing sustained release microcapsules according to claim 1, wherein the aqueous solution and the oily solution are fed into and removed from the first mixer continuously so that the residence time of the solutions in the first mixer is less than 7 seconds.

9. The process for producing sustained release microcapsules according to claim 1, wherein the first mixer is of cylindrical shape and comprises a first mixing element for agitation.

10. The process for producing sustained release microcapsules according to claim 9 wherein the first mixing element is a rotor-grooved stator assembly.

11. The process for producing sustained release microcapsules according to claim 10, wherein the rotor peripheral speed is greater than 3 m/sec.

12. The process for producing sustained release microcapsules according to claim 1, wherein the second mixer is of cylindrical shape and comprises a second mixing element for agitation.

13. The process for producing sustained release microcapsules according to claim 12 wherein the second mixing element is a rotor-grooved stator assembly.

14. The process for producing sustained release microcapsules according to claim 9, wherein the first mixing element is a sonic mixing probe.

15. The process for producing sustained release microcapsules according to claim 12, wherein the first emulsion and the aqueous phase containing a protective hydrophilic colloid are fed into and removed from the second mixer continuously so that the residence time of the solutions in the second mixer is less than 1 seconds and wherein the peripheral rotor speed of the rotor-stator assembly of the second mixer is greater than 9 m/sec.

16. The process for producing sustained release microcapsules according to claim 1, wherein the first mixer comprises an intensive agitator element and an inner tube and wherein the intermixing of the active peptide aqueous solution with the oily polymer phase to form an emulsion comprises injecting both solutions coaxially to the agitator element axis, in the front face of the first intensive agitation equipment, with the aqueous solution entering by the inner tube at a distance from the agitator device not greater than 20 mm.

17. The process for producing sustained release microcapsules according to claim 1, wherein the total feed flow to the first mixer is from about 30 to 500 ml/min.

18. The process for producing sustained release microcapsules according to claim 1, wherein the oily solution of the biodegradable polymer and the aqueous phase containing the active peptide are fed into the first mixer at a mass ratio of about 6:10.

19. The process for producing sustained release microcapsules according to claim 1, wherein the total feed flow to the second mixer is from about 500 to 10,000 ml/min.

20. The process for producing sustained release microcapsules according to claim 1, wherein the intermixing of the first water/oil emulsion into the aqueous phase comprises injecting both flows coaxially to the axis of the agitating element, in the front face of the second intensive agitation equipment, and with the water/oil emulsion entering by the inner tube, at a distance from the agitating device not greater than 20 mm.

21. The process for producing sustained release microcapsules according to claim 1, wherein the aqueous phase and the first emulsion are fed to the second mixer at a mass ratio from about 30:80.

22. The process for producing sustained release microcapsules according to claim 1, wherein the retention substance is a gelatin of bovine origin with a gelation power from about Bloom 75 to Bloom 100, type B, and wherein the gelatin is added to the aqueous solution of the active peptide at a concentration ranging from 0% to 10% in weight.

23. The process for producing sustained release microcapsules according to claim 1, wherein the biodegradable polymer is a copolymer of d,l-lactic acid and glycolic acid, of a molecular weight from about 10,000 to 30,000 Daltons.

24. The process for producing sustained release microcapsules according to claim 19, wherein the molar ratio of the lactic:glycolic acid monomers ranges from 50:50 to 100:0.

25. The process for producing sustained release microcapsules according to claim 1, wherein the organic solvent in the biodegradable polymer organic solution comprises methylene chloride.

26. The process for producing sustained release microcapsules according to claim 1, wherein the protective hydrophilic colloid in the aqueous phase comprises polyvinyl alcohol (PVA) having an apparent viscosity of 25 to 50 centipoise as measured in a 4% by weight aqueous solution at a temperature of 20° C., with an hydrolysis grade from about 85% to 89% and a concentration from about 0.1% to 1% by weight.

27. The process for producing sustained release microcapsules according to claim 1, wherein the lyophilization excipient is mannitol at a concentration from about 0.1 to 5% by weight in the suspension.

28. The process for producing sustained release microcapsules according to claim 1, wherein the microcapsules which have been dispersed into an aqueous phase are dispersed into a vessel suitable for a final dosage, and the aqueous phase in the vessel is frozen in an orbital agitation freezer at temperatures below −20° C., over a period of from 5 to 60 min.

29. The process for producing sustained release microcapsules according to claim 1, wherein the orbital agitation freezer used for freezing is a refrigerated plate with an orbital circular movement where the rotation radius is less than or equal to the radius of the base of the vessel that contains aqueous dispersion of microcapsules.

30. The process for producing sustained release microcapsules according to claim 1, wherein the agitator device makes an orbital circular movement, with a rotation speed from about 20 to 50 r.p.m.

31. The process for producing sustained release microcapsules according to claim 1, wherein the dispersion of microcapsules into an aqueous medium and the subsequent freezing with agitation operations are made in a closed system.

32. The process for producing sustained release microcapsules according to claim 1, wherein the microcapsules, once produced, retain substantially the same size and size distribution and the same active peptide concentration during the entire process.

33. The process for producing sustained release microcapsules according to claim 1, wherein the flow rates of the substances fed to the first and second mixers are independently adjusted.

34. The process for producing sustained release microcapsules according to claim 1, wherein the intensity of the mixing in the first and second mixers are adjusted independently of each other and of the feed flow rates of the substances fed to the mixers.

35. The process for producing sustained release microcapsules according to claim 1, wherein the active peptide is leuprolide acetate.

36. The process for producing sustained release microcapsules according to claim 1, wherein the active peptide is goserelin acetate.

37. The process for producing sustained release microcapsules according to claim 1, wherein the active peptide is nafarelin acetate.

38. The process for producing sustained release microcapsules according to claim 1, wherein the active peptide is triptorelin acetate.

39. The process for producing sustained release microcapsules according to claim 1 wherein the active peptide is buserelin acetate.

40. The process for producing sustained release microcapsules according to claim 1, wherein the active peptide percentage loss in the process is less than 30% of the raw material.

41. The process for producing sustained release microcapsules according to claim 1, wherein the vessel is a dosage vial which after lyophilization is sealed to prepare the final product for consumption.

42. The process for producing sustained release microcapsules according to claim 1, wherein the vessels is a container suitable for bulk sales.

43. The process for producing sustained release microcapsules according to claim 1, wherein the microcapsules resulting from this procedure are not susceptible to agglomeration during a normal period before use, and the suspension reconstitution to be injected is instantaneous.

44. The process for producing sustained release microcapsules according to claim 1, wherein the process can designed so that the microcapsules provide a period of sustained release of the water soluble peptides that is adjustable from about 1 week to about 18 weeks.

45. A microcapsule for the sustained release of water soluble peptides, which microcapsule is produced by the method according to claim 1.

46. A formulation comprising a microcapsule according to claim 41 and other materials 1.

47. A process for producing microcapsules for the sustained release of water soluble peptides, the microcapsules having an adjustable release period between about 1 to about 18 weeks, the process comprising the steps of:

continuously feeding, using a first set of dosing apparatuses, an aqueous solution comprising a water-soluble active peptide and a retention substance and an oily solution comprising a biodegradable polymer in an organic solvent that is insoluble or only slightly soluble in water, into a first mixer that is closed to the atmosphere and subjecting the aqueous and oily solution to intense agitation to produce a first emulsion;

withdrawing continuously from the first mixer said first emulsion and cooling it;

continuously feeding, using a second set of dosing apparatuses said first emulsion and an aqueous phase containing a protective hydrophilic colloid into a second mixer that is closed to the atmosphere and subjecting the first emulsion and the aqueous phase containing the colloid to intense agitation to produce a second emulsion;

continuously withdrawing the second emulsion from the second mixer and feeding it into a closed vessel for removing the organic solvent from the second emulsion by reducing the pressure in the closed vessel, thereby producing microcapsules of distributed sizes, the microcapsules containing the water soluble peptide;

adjusting the size distribution of the microcapsules by sieving, centrifuging and washing the microcapsules;

dispersing the microcapsules in an aqueous medium containing a lyophilization excipient;

distributing the aqueous dispersion of microcapsules into a plurality of vessels and freezing the aqueous medium containing the lyophilizing excipient and the microcapsules at a temperature of less than about $-20°$ C. in an orbital agitation freezer; and lyophilizing the frozen microcapsule dispersion.

* * * * *